US005906589A

United States Patent [19]

Gordon et al.

[11] Patent Number: 5,906,589

[45] Date of Patent: May 25, 1999

[54] METHOD AND APPARATUS FOR OCCLUSION MONITORING USING PRESSURE WAVEFORM ANALYSIS

[75] Inventors: Timothy M. Gordon, Lakewood; Stephen K. Scovill, Golden; Peter Fletcher-Haynes, Bailey; Scott Martin, Lakewood, all of Colo.

[73] Assignee: COBE Laboratories, Inc.

[21] Appl. No.: 08/747,852

[22] Filed: Nov. 13, 1996

[51] Int. Cl.[6] ..... A61M 31/00

[52] U.S. Cl. ..... 604/65; 604/48; 604/131

[58] Field of Search ..... 604/65, 131, 66, 604/67, 4, 5, 6, 48, 30

[56] References Cited

U.S. PATENT DOCUMENTS

| | | | |
|---|---|---|---|
| 4,605,503 | 8/1986 | Bilstad et al. | 210/651 |
| 4,657,529 | 4/1987 | Prince et al. | 604/6 |
| 4,894,164 | 1/1990 | Polaschegg | 210/646 |
| 4,897,185 | 1/1990 | Schuyler et al. | 210/90 |
| 4,935,002 | 6/1990 | Gordon | 604/4 |
| 4,950,235 | 8/1990 | Slate et al. | 604/65 |
| 5,112,298 | 5/1992 | Prince et al. | 604/6 |
| 5,147,290 | 9/1992 | Jonsson | 604/5 |
| 5,178,603 | 1/1993 | Prince | 604/6 |
| 5,227,049 | 7/1993 | Chevallet et al. | 210/97 |
| 5,386,734 | 2/1995 | Pusinelli | 73/863.21 |
| 5,387,187 | 2/1995 | Fell et al. | 604/6 |
| 5,437,624 | 8/1995 | Langley | 604/4 |
| 5,494,578 | 2/1996 | Brown et al. | 210/360.1 |
| 5,494,592 | 2/1996 | Latham, Jr. et al. | 210/805 |
| 5,536,237 | 7/1996 | Prince et al. | 604/4 |

FOREIGN PATENT DOCUMENTS

| | | |
|---|---|---|
| 0 328 162 A2 | 8/1989 | European Pat. Off. . |
| 0 431 310 A1 | 6/1991 | European Pat. Off. . |
| WO 92/20383 | 11/1992 | WIPO . |

*Primary Examiner*—Wynn Wood Coggins
*Assistant Examiner*—N. Kent Gring
*Attorney, Agent, or Firm*—Sheridan Ross P.C.

[57] ABSTRACT

A method and apparatus for occlusion monitoring in a flow circuit using pressure waveform analysis. The flow circuit includes a first conduit and a second conduit which fluidly interconnects a fluid supply with the first conduit. A pump is disposed in an intermediate portion of the second conduit. Monitoring of the pressure in the first conduit is used to identify any occlusions in that portion of the second conduit which is disposed between the pump and the fluid supply.

40 Claims, 5 Drawing Sheets

5
10
15
65
100
60
70
105
95
80
90
85
20
40
25
45
50
30
35
75

METHOD AND APPARATUS FOR OCCLUSION MONITORING USING PRESSURE WAVEFORM ANALYSIS

FIELD OF THE INVENTION

The present invention generally relates to monitoring for occlusions in a flow circuit and, more specifically, to monitoring for occlusions in a conduit of a flow circuit using pressure waveform analysis, the conduit being at least at times effectively isolated from a pressure sensing device used to generate the pressure waveform.

BACKGROUND OF THE INVENTION

Blood apheresis systems withdraw blood from a donor/patient and separate the blood into various blood components (e.g., red blood cells, white blood cells, platelets, plasma). Some of these blood components are collected and others are returned to the donor/patient.

In many apheresis systems, blood is withdrawn from the donor/patient through a blood inlet line by a blood inlet pump. Anticoagulant (hereinafter sometimes referred to as "AC") is introduced into the blood inlet line at a location which is between the donor/patient and the blood inlet pump. The amount of anticoagulant provided to the blood is important. Introducing less than the desired amount of anticoagulant increases the potential for blood clotting which may adversely affect the apheresis procedure and more importantly the donor/patient. Reductions in the flow of anticoagulant into the blood may be due to an occlusion in the AC inlet line (the line which caries AC to the blood inlet line).

A number of approaches are available to identify occlusions in the flow circuit of a blood apheresis system. Some blood apheresis systems use an electronic drip counter or bag weighing system to control the flow of anticoagulant into the blood. In this case an occlusion in the AC line would be "displayed" to the operator in the nature of there being less "drips" of anticoagulant than normal. Other systems use a pressure sensor in the blood inlet line between the donor/patient and the blood inlet pump to detect for a collapsing of the vein of the donor/patient. Cost considerations are of course always an issue in determining which approach to take for occlusion monitoring in the flow circuit of a blood apheresis system, as increasing the overall cost of the blood apheresis system may have a significant effect on its commercial success.

SUMMARY OF THE INVENTION

The present invention may be characterized as relating to monitoring for an occlusion in a conduit of a flow circuit using pressure waveform analysis. A first aspect of the present invention relates to a flow circuit which includes a first conduit, a fluid supply, a second conduit extending between the fluid supply and a first location on the first conduit at which the first and second conduits are fluidly connected, and a pump which is disposed between the end of the second conduit where it interfaces with the first conduit (e.g., at the first location) and the end of the second conduit where it interfaces with the fluid supply. The pressure is monitored at a second location of the first conduit (e.g., downstream of the first location or in the direction of the flow through the first conduit) by an appropriate pressure sensing device as fluid from the fluid supply is pumped into the first conduit through the second conduit. It should be appreciated that there may be a flow through the first conduit from a source other than the fluid supply such that there is a merger of at least two flows at the first location in the first conduit. By monitoring the pressure in the first conduit at the second location, the first aspect of the present invention monitors for an occlusion of any portion of the second conduit which is disposed between the fluid supply and the pump. Detection of an occlusion in the second conduit through this pressure monitoring may then activate some type of an alarm and/or display to apprise an operator of the occluded condition.

In one embodiment of this first aspect, the pump is a peristaltic pump with one or more rollers (e.g., two rollers, three rollers) which each progressively occlude the second conduit to pump fluid therethrough on a sequential basis. As each roller of the peristaltic pump occludes the second conduit, the fluid supply and the portion of the second conduit which is disposed between the pump and the fluid supply is substantially isolated from the first conduit and including the second location where the pressure is being monitored in the first conduit. If there is an occlusion in any portion of the second conduit between the pump and the fluid supply ("a first occlusion"), operation of the pump will generate a negative pressure in a portion of the second conduit which is used to identify the existence of the first occlusion. Specifically, as each roller of the pump progressively occludes the second conduit, a negative pressure will be created in at least a portion of the second conduit between the first occlusion and the occluding roller since the pump can no longer draw from the fluid supply. If two rollers of the pump simultaneously occlude the second conduit at two displaced positions, the negative pressure used by the present invention will be located in that part of the second conduit between the occluding rollers. When each roller of the peristaltic pump loses occlusion with the second conduit at the end of its "stroke", the negative pressure in at least a portion of the second conduit between the occluding roller and the first occlusion will draw fluid back toward the first occlusion. This "drawn" fluid will come from that portion of the second conduit which is between pump and the first location where the second conduit interconnects with the first conduit, and from the first conduit as well. Therefore, there will then be a corresponding drop in the pressure at the first location of the first conduit. By knowing the speed of the peristaltic pump (i.e., its rotational velocity) and the number of rollers of the peristaltic pump, the existence of the first occlusion in the portion of the second conduit between the pump and the fluid supply will produce a certain waveform. This certain waveform is one in which there are a plurality of pressure drops or spikes of at least a certain magnitude and/or width (e.g., the width being used to differentiate pressure drops or spikes associated with the first occlusion from noise in the flow circuit), and in which the time between adjacent pressure drops or spikes of this magnitude corresponds with the inverse of rotational speed of the peristaltic pump multiplied by its number of rollers (i.e., 1/(pump speed×number of rollers). Occlusions of varying degrees may be detected in this manner (e.g., 100% occlusions or a no flow condition, 50% occlusions or a ½ flow condition, and at least a 28% occlusion or where the flow is reduced by at least 28%). Moreover, this technique may be applicable to flow circuits using pumps other than those of the peristaltic type.

Other variations of the above-noted first aspect exist. For instance, a waveform may be generated with corresponds with the pressure at the second location in the first conduit, and further this may be effectively compared with a waveform which is indicative of an occlusion in any portion of the second conduit located between the pump and the fluid supply. A signal which corresponds with the pressure at the second location in the first conduit may be generated which is computer-readable and/or this signal may be processed in some manner to account for noise in at least part of the flow circuit and/or to accentuate the pressure drops or spikes associated with an occlusion in any portion of the second conduit between the pump and the fluid supply (e.g., using an adaptive filtering technique, using a synchronized average detection technique).

A second aspect of the present invention relates to an application of that described above, and more specifically relates to an extracorporeal blood processing system which utilizes the foregoing principles. The above-noted first conduit is a blood inlet line which allows blood from a blood supply (e.g., a donor/patient) to be provided to a blood processing device (e.g., a centrifuge for blood component separation). The above-noted fluid supply is an anticoagulant (AC) supply, the above-noted second conduit is an anticoagulant or AC line, and the above-noted pump is an anticoagulant or AC pump. By monitoring the pressure in the blood inlet conduit as blood is being pumped from the blood supply to the blood processing device, occlusions in the AC line between the AC pump and the AC supply may be detected in accordance with the foregoing principles.

DETAILED DESCRIPTION

The present invention will be described in relation to the accompanying drawings which assist in illustrating its various features. One application of the present invention is to use pressure waveform analysis to identify an occlusion in an extracorporeal blood processing system, although it will be appreciated after a review of the following that principles of the present invention may be applicable in other flow circuits as well.

Figure 1:
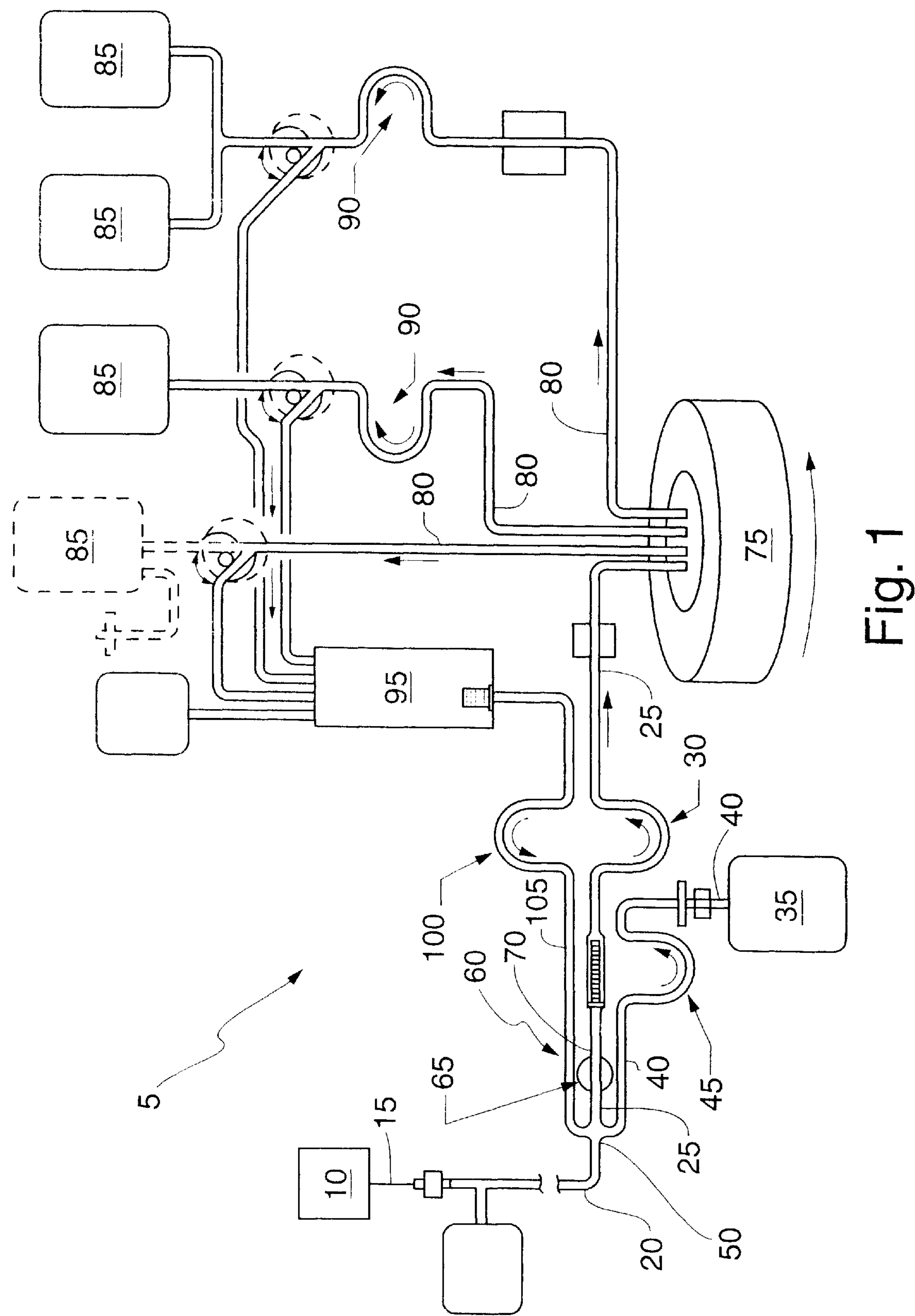
FIG. 1 is a schematic view of one embodiment of a blood apheresis system.

The blood apheresis system 5 of FIG. 1 is an extracorporeal blood processing system which interfaces with a blood supply 10 which will typically be a human donor/patient, although it could merely be a container of blood (hereafter donor/patient 10). An access needle 15 interfaces with the donor/patient 10 and fluidly interconnects the donor/patient 10 with access tubing 20. The system 5 is for a single needle procedure as blood is both removed from the donor/patient 10 and blood or components thereof are provided back to the donor/patient 10 through this same access tubing 20. This alleviates the need for puncturing a donor/patient 10 at more than one location. After a review of the following, it will be appreciated that principles of the present invention will be equally applicable to a dual needle procedure as well (i.e., where one access needle is used for drawing blood from the donor/patient and a second access needle is used for returning blood to the donor/patient).

The access tubing 20 interconnects with blood inlet tubing 25 which provides blood from the donor/patient 10 to a centrifuge 75 via the action of a peristaltic-type inlet pump 30 on the blood inlet tubing 25. In order to reduce the potential for clotting of the blood between the time it is removed from the donor/patient 10 and the time at which the blood or components thereof are returned back to the donor/patient 10, anticoagulant (hereinafter sometimes referred to as "AC") is introduced into the blood. This anticoagulant is contained within an anticoagulant or AC container 35 which is fluidly interconnected with the access tubing 20 and blood inlet tubing 25 at a first location 50 via anticoagulant or AC tubing 40. An anticoagulant or AC pump 45 of the peristaltic type acts on the AC tubing 40 to pump anticoagulant from the AC container 35 into the blood inlet tubing 25 and/or the access tubing 20 at the first location 50. Certain specifics of the AC pump 45 will be discussed in more detail below.

Blood within the centrifuge 75 is separated into a plurality of components which may be separately removed from the centrifuge 75 for collection and/or for return to the donor/patient 10. Details of one embodiment of an appropriate configuration for the centrifuge 75 is disclosed in U.S. Pat. No. 4,387,848 to Kellog et al., entitled "CENTRIFUGE ASSEMBLY", and issued Jun. 14, 1983, the entire disclosure of which is hereby incorporated by reference herein. Generally, a number of centrifuge outlet tubings 80 extend from the centrifuge 75 to direct the separated blood components to separate collection containers 85. A number of peristaltic-type collection pumps 90 may be utilized to facilitate the removal of these components from the centrifuge 75.

Components which are to be returned to the donor/patient 10 are directed to a return reservoir 95. The return reservoir 95 includes a high level detector (not shown). When the high level detector senses blood components in the return reservoir 95 at a predetermined level, an activating signal is sent to a return pump 100. The inlet pump 30 may be simultaneously shut off at this time or the speed of the return pump 100 may simply be selected to be greater than the inlet pump 30 to "override" the effect of the inlet pump 30 at this time. Activation of the return pump 100 removes blood components from the return reservoir 95 and provides these back to the access tubing 20 and then to the donor/patient 10 via return tubing 105 which interconnects with access tubing 20. The return pump 100 is deactivated when a low level detector (not shown) in the return reservoir 95 is activated or when the low level detector senses that the level of components in the reservoir 95 has reached a predetermined level in the return reservoir 95. Thereafter, another draw cycle may be initiated until the apheresis procedure is completed.

The various pumps 30, 45, 90, and 100 are each of the peristaltic type in the blood apheresis system 5. One design of a peristaltic pump which may be used is disclosed in detail in U.S. Pat. No. 5,263,831, the entire disclosure of which is incorporated by reference in its entirety herein. Three views of this pump are presented in FIGS. 2A–C in relation to the AC pump 45. The AC pump 45 generally includes a rotatable rotor 145 having two rollers 175 which are each freely, rotatably mounted on the rotor 145. Peristaltic-type pumps having at least one, and typically at least two rollers will utilized for the AC pump 45 (e.g., a three roller pump). The rotor 145 is disposed within a cavity 180 of a stator or housing 150. The border of this cavity 180 defines a raceway 155 with an inlet 165 and an outlet 170. The AC tubing 40 is flexible and compressible, and is loaded into the AC pump 45 between the raceway 155 and the rollers 175 which are biased out toward the raceway 155. The material and/or wall thickness of the AC tubing 40, and/or the biasing forces generated by the rollers 175 may be selected such that the rollers 175 totally occlude the AC tubing 40.

Figure 2A:
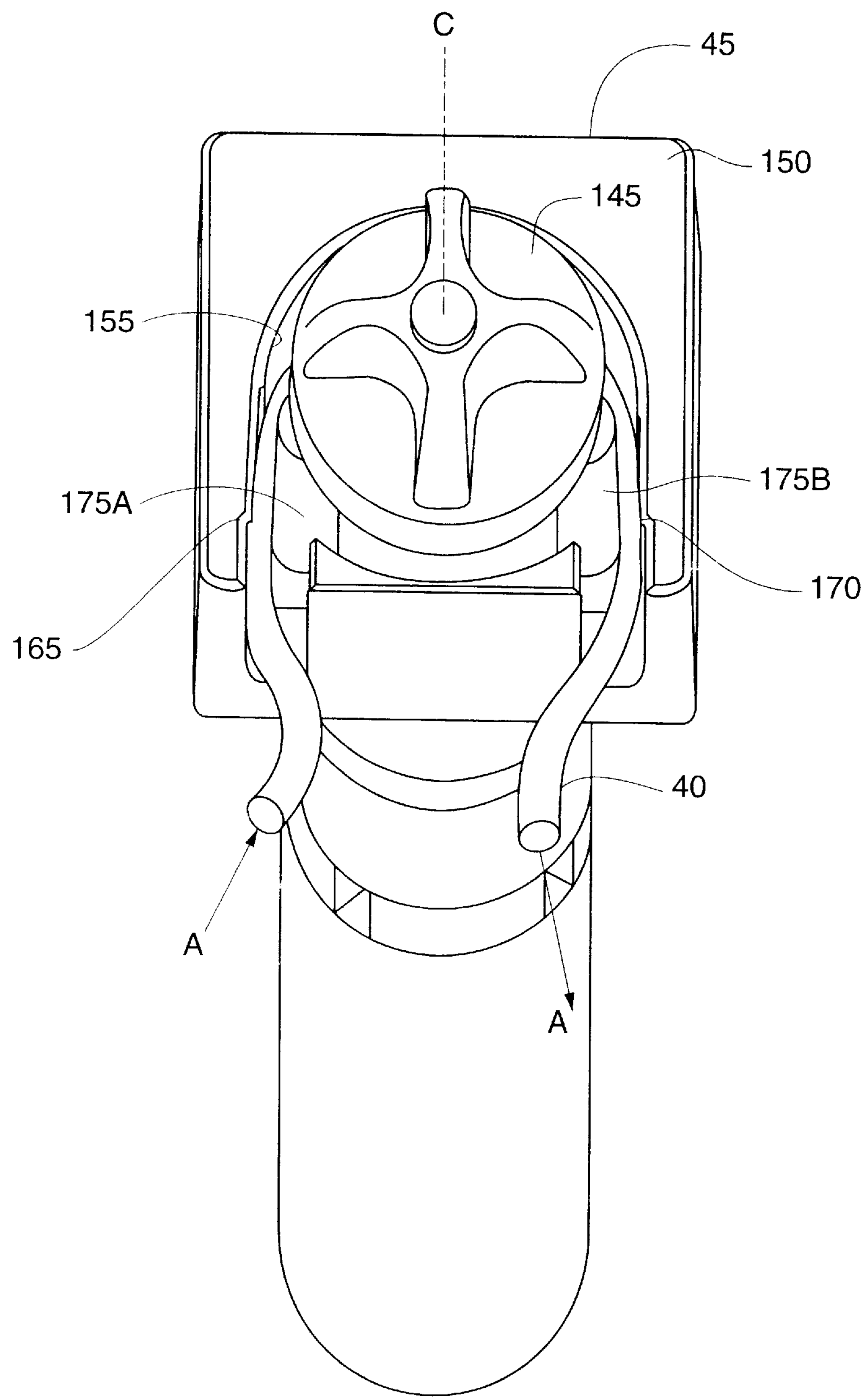
FIG. 2A is a perspective view of one embodiment of a peristaltic pump which may be used in the system of FIG. 1.
Figure 2B:
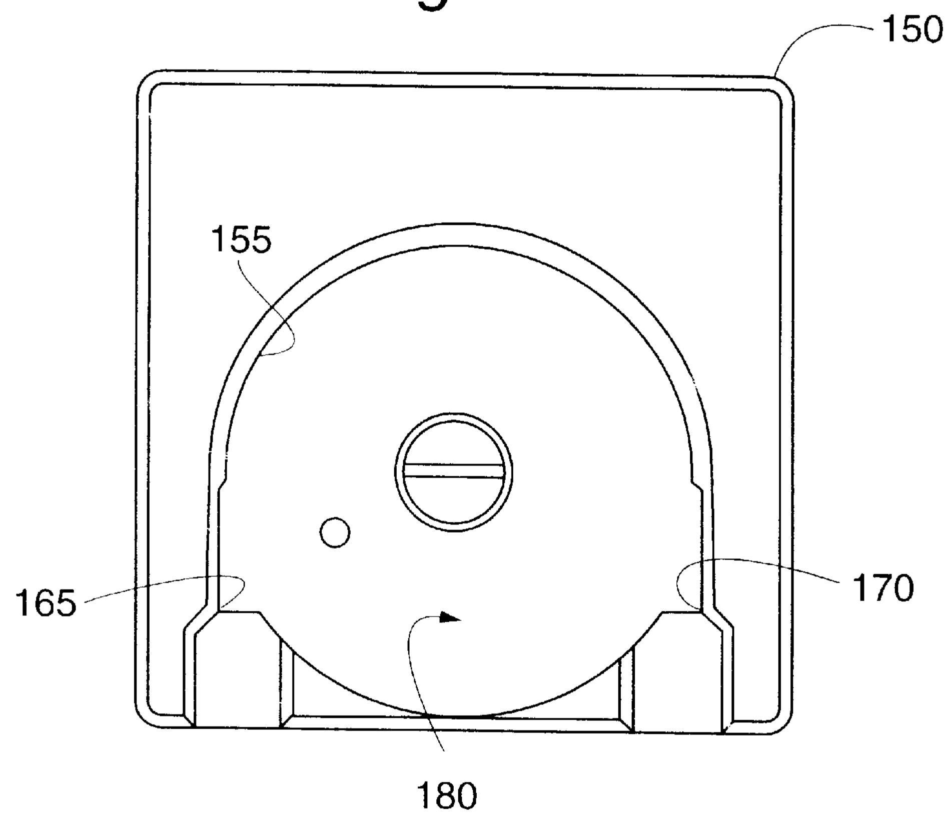
FIG. 2B is a top view of the stator of the pump of FIG. 2A.
Figure 2C:
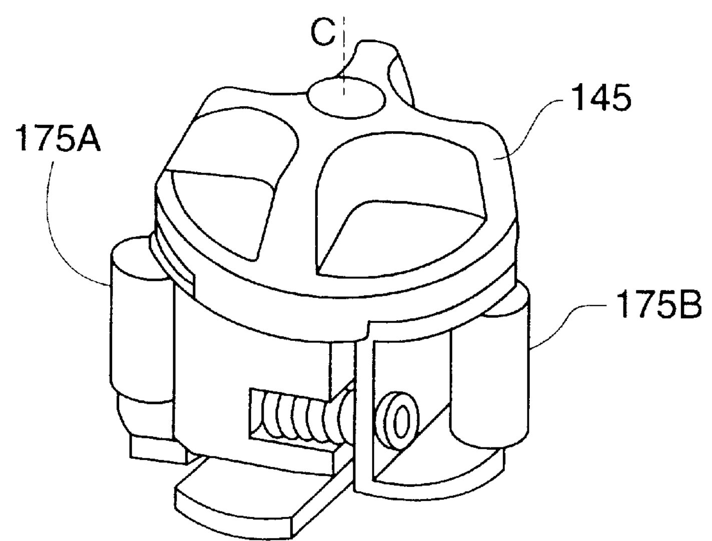
FIG. 2C is a perspective view of the rotor of the pump of FIG. 2A.

Rotation of the rotor 145 in a clockwise direction as illustrated in FIG. 2A results in a flow through the AC tubing 40 in the direction of the arrow A. Roller 175A begins occluding the AC tubing 40 at the inlet 165 and "moves" the liquid contained between the rollers 175A and 175B by progressively occluding the AC tubing 40 via rotation of the rotor 145. When roller 175A reaches the outlet 170, the roller 175A moves away from the raceway 155 and discontinues occluding the AC tubing 40. At this same time roller 175B reaches the pump inlet 165 and begins occluding the AC tubing 40 to continue the pumping action in the noted manner. As such, the AC tubing 40 is sequentially and progressively occluded by the AC pump 45. Although a direction of rotation of the rotor 145 of the AC pump 45 is referred to herein, it should be appreciated that in a given apheresis system, the AC pump 45 may actually rotate in a counter-clockwise direction.

The blood apheresis system 5 has the ability to monitor and detect occlusions in that portion of the AC tubing 40 which is disposed between the AC pump 45 and the AC container 35 (hereafter sometimes referred to as the "upstream" portion of the AC tubing 40). An AC occlusion monitoring system 60 includes a pressure sensing device 65 which monitors the pressure in the blood inlet tubing 25 at a second location 70. The second location 70 is downstream of the first location 50 in relation to a draw cycle, or stated another way the second location 70 is disposed between the blood inlet pump 30 and the first location 50 which is again where the AC tubing 40 joins the blood inlet tubing 25 and the access tubing 20. Appropriate pressure sensing devices 65 include load cells, pressure transducers (i.e., CDX type), strain gauge force cells, pressure diaphragm transducers, with the mechanically coupled load cells being preferred.

Figure 3:
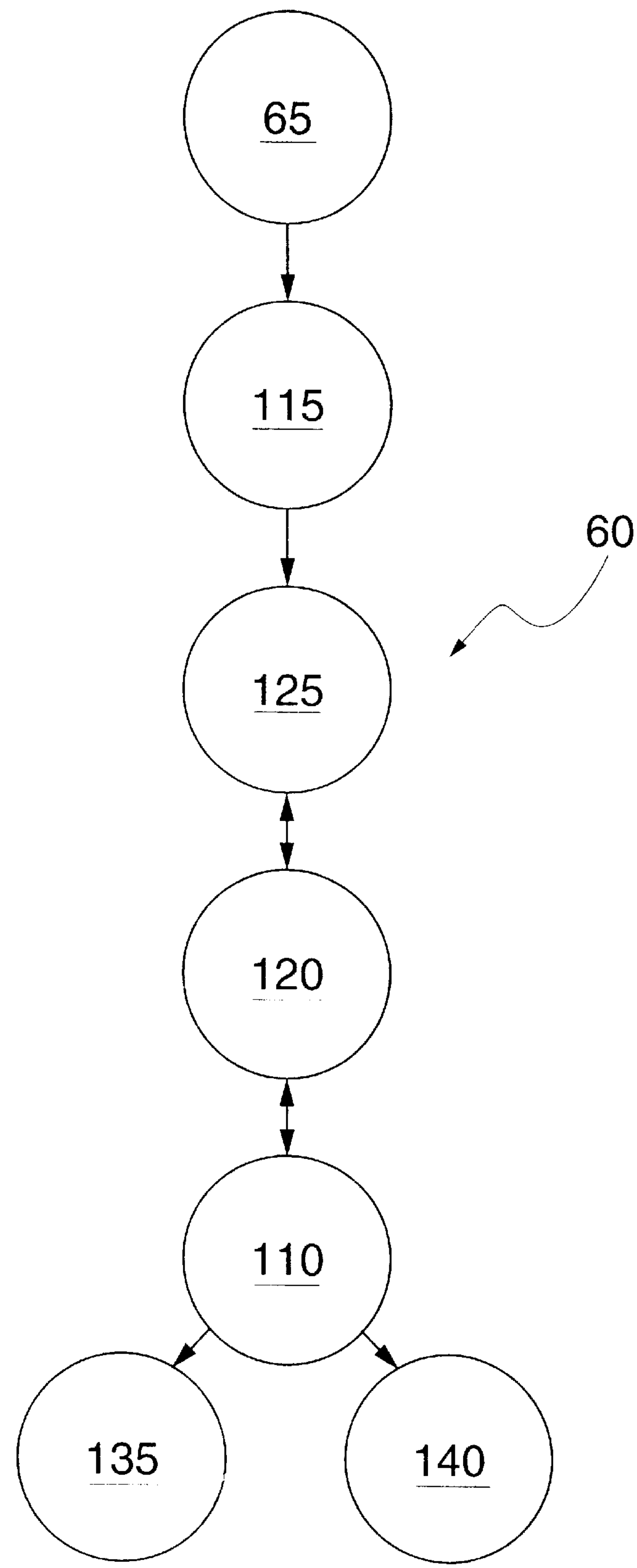
FIG. 3 is a flow chart of an occlusion monitoring system used by the apheresis system of FIG. 1.

Components of the AC occlusion monitoring system 60 are more specifically identified in FIG. 3. In addition to the pressure sensing device 65, the AC occlusion monitoring system 60 further includes a converter 115 to convert the analog signal from the pressure sensing device 65 to a digital signal. The signal from the converter 115 may then be processed at a signal processor 125 to process the signal so as to reduce the effects of noise in the system 5 on the monitoring system 60, principally noise from the blood inlet pump 30. Various signal processing techniques may be utilized, including using various filtering techniques (e.g., adaptive filtering techniques which only let a signal of a predetermined magnitude pass through the filter) and synchronized averaged detection techniques which use a CPU 120 to generate an averaged pressure signal from the pressure sensing device 65. The processed signal is then evaluated by a waveform analyzer 110 which interfaces with/utilizes the CPU 120. This waveform analyzer 110 effectively monitors the output from the pressure sensing device 65 and provides a signal to an alarm 135 and/or a display 140 when an occlusion is detected in any portion of the AC tubing 40 between the AC pump 45 and the AC container 35.

The waveform analyzer 110 generally evaluates signals from the pressure sensing device 65 which correspond to the pressure in the blood inlet tubing 25 at the second location 70 and which are provided to the waveform analyzer 110 on a periodic basis. In one embodiment, the pressure sensing device 65 sends a signal to the waveform analyzer 110 at least about every 20 milliseconds. The waveform analyzer 110 effectively monitors this signal to identify a pressure waveform or pattern which is indicative of/corresponds with an occlusion in any portion of AC tubing 40 between the AC pump 45 and the AC container 35. The waveform analyzer 110 may be initialized in a variety of ways to provide this general function.

Figure 4:
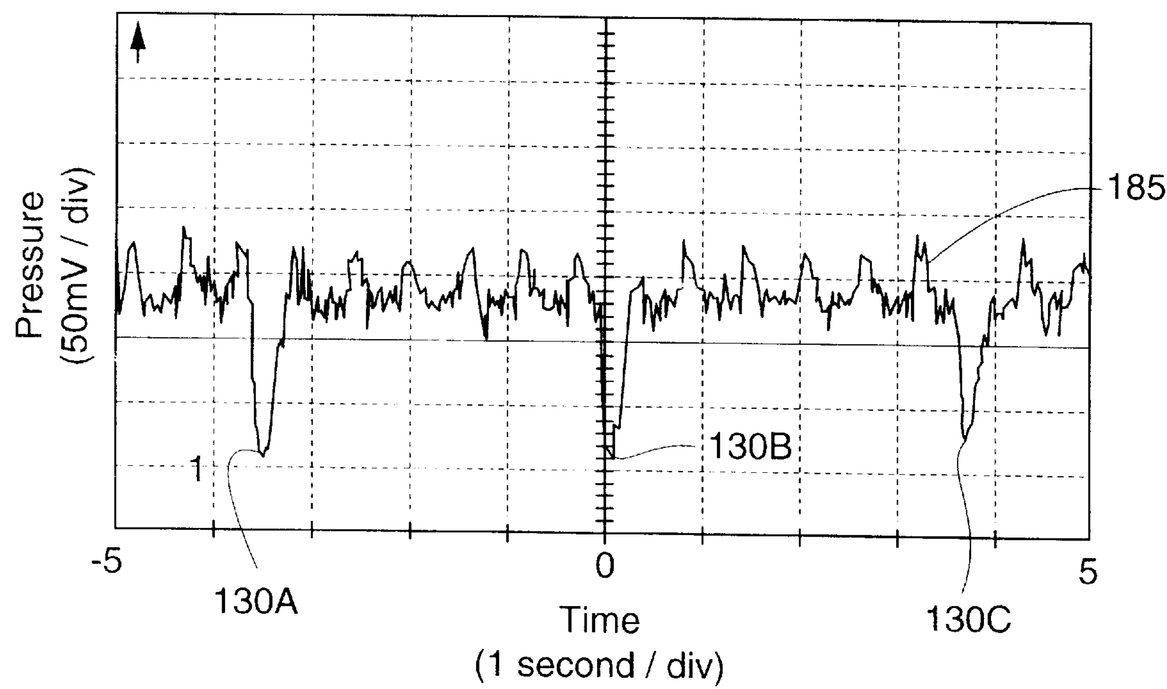
FIG. 4 is one embodiment of a waveform analyzer which may be used by the occlusion monitoring system of FIG. 3.

The waveform analyzer 110 may be initialized or configured to identify a condition such as that illustrated by the waveform 185 presented in FIG. 4. This is referred to as a simple detection technique. The waveform 185 corresponds with an occlusion in that portion of the AC tubing 40 between the AC pump 45 and the AC container 35. Generally, there are a plurality of pressure drops/spikes 130 in the waveform 185 which are separated by a time period which relates to the speed of the AC pump 45. Information which is required for the waveform analyzer 110 to identify that the waveform 185 corresponds with an occlusion in the AC tubing 40 between the AC pump 45 and the AC container 35 are the speed of the AC pump 45 (i.e., its rotational velocity) and the number of rollers 175 used by the AC pump 45 (i.e., two in the FIG. 2A embodiment). From this information the waveform analyzer 110 can compute the number of occlusions per unit of time the AC pump 45 will produce on the AC tubing 40 (i.e., by multiplying the speed of the AC pump 45 by the number of rollers 175 used by the pump 45). This information allows the waveform analyzer 110 to identify an occlusion in the AC tubing 40 between the AC pump 45 and the AC container 35 due to the effect that the periodic occlusion of the AC tubing 40 by the AC pump 45 will have on the pressure in the blood inlet tubing 25 at the second location 70 and as monitored by the pressure sensing device 65.

The AC pump 45 again has an inlet 165 where the AC tubing 40 from the AC container 35 effectively enters the AC pump 45 as illustrated in FIG. 2A. The AC tubing 40 is disposed between the rollers 175 and the raceway 155 and leaves the pump 45 at its exit 170 where the AC tubing 40 continues to the first location 50 to join with the access tubing 20 and the blood inlet tubing 25. As roller 175A of the AC pump 45 occludes the AC tubing 40 against the raceway 155, each of the AC container 35 and that portion of the AC tubing 40 located between the roller 175A and the AC container 35 are substantially isolated from each of the access tubing 20, the blood inlet tubing 25, and the pressure sensing device 65.

Consider the situation now where there is a complete occlusion of the AC tubing 40 upstream of the AC pump 45 or between the AC pump 45 and the AC container 35 (hereafter a "first occlusion") (i.e., a "no flow" condition from the AC container 35 to the AC pump 45 through the AC tubing 40). In this case, as the roller 175A progressively occludes the AC tubing 40 by rotation of the rotor 145 in the clockwise direction illustrated in FIG. 2A, a negative pressure will be created in that portion of the AC tubing 40 which is disposed between the roller 175A and first occlusion in the AC tubing 40 since the AC pump 45 can no longer draw anticoagulant from the AC container 35. When the roller 175A of the AC pump 45 reaches the exit 170 and it discontinues occluding the AC tubing 40 or releases the "pump" occlusion, the negative pressure in the portion of the AC tubing 40 between the roller 175A and first occlusion will then draw fluid back toward the first occlusion in the AC tubing 40. This fluid will come from that portion of the AC tubing 40 which is downstream of the AC pump 45 or that portion of the AC tubing 40 which is disposed between the AC pump 45 and the first location 50. Moreover, the noted negative pressure will also draw fluid from the blood inlet tubing 25 and/or the access tubing 20 back toward the first occlusion in the AC tubing 40 between the AC pump 45 and the AC container 35. This produces a corresponding pressure drop in the blood inlet tubing 25 at the second location 70 which is sensed by the pressure sensing device 65. The pressure sensing device 65 sends a signal corresponding with this pressure drop to the waveform analyzer 110. This pressure drop corresponds with pressure drop/spike 130A on the waveform 185 illustrated in FIG. 4.

The roller 175B of the AC pump 45 effectively begins to occlude the AC tubing 40 against the raceway 155 at the same time that the roller 175A of the AC pump 45 discontinues occluding the AC tubing 40 against the raceway 155. Release of the occlusion in the AC tubing 40 by the roller 175A again produced the pressure drop/spike 130A due to the existence of the first occlusion in the AC tubing 40 between the AC pump 45 and the AC container 35. Occlusion of the AC tubing 40 by the roller 175B, as in the case of the roller 175A, substantially isolates the AC container 35 from the access tubing 20, the blood inlet tubing 25, and the pressure sensing device 65. As the roller 175B progressively occludes the AC tubing 40 by rotation of the rotor 145 in the clockwise direction illustrated in FIG. 2A, a negative pressure again will be created in that portion of the AC tubing 40 which is located between the roller 175B and the first occlusion in the AC tubing 40 since the AC pump 45 can no longer draw anticoagulant from the AC container 35. When the roller 175B of the AC pump 45 reaches the exit 170 and it discontinues occluding the AC tubing 40 or releases the "pump" occlusion, the negative pressure in the portion of the AC tubing 40 between the roller 175B and first occlusion will again then draw fluid back toward the first occlusion. This fluid comes from that portion of the AC tubing 40 which is downstream of the AC pump 45 or that portion of the AC tubing 40 which is disposed between the AC pump 45 and the first location 50. Moreover, this negative pressure will also again draw fluid from the blood inlet tubing 25 and/or the access tubing 20 back toward the first occlusion in the AC tubing 40. This produces a corresponding pressure drop in the blood inlet tubing 25 at the second location 70 which is again sensed by the pressure sensing device 65. The pressure sensing device 65 provides a signal corresponding with this pressure drop to the waveform analyzer 110. This pressure drop corresponds with pressure drop/spike 130B on the waveform 185 illustrated in FIG. 4.

The pressure drop/spike 130B is separated from the pressure drop/spike 130A by a time period which corresponds with the inverse of twice the speed of the AC pump 45 since there are two rollers 175 and thereby two pump occlusions of the AC tubing 40 on each revolution of the rotor 145 of the AC pump 45. This pattern will keep repeating when there is an occlusion in the AC tubing 40 between the AC pump 40 and the AC container 30 due to the periodic occlusion of the AC tubing 40 by the rollers 175 of the AC pump 45. When this type of pattern is recognized by the waveform analyzer 110, it will provide a signal to the alarm 135 and/or the display 140 to provide an indication to the operator of the apheresis system 5 of the AC occlusion condition.

Summarizing the situation where the waveform analyzer 110 uses a simple detection technique, a pattern or waveform which is indicative of/corresponds with an occlusion in that portion of the AC tubing 40 which is located between the AC pump 45 and the AC container 35 is one in which there are a plurality of pressure drops/spikes 130 of at least a certain magnitude and/or width, and in which the time between adjacent pressure drops/spikes 130 of this magnitude corresponds with the inverse of the product of rotational speed of the AC pump 45 and the number of rollers 175 used by the pump 45 (i.e., 1/(the speed of the pump 45 multiplied by the number of rollers 175)). In the example presented in FIG. 4, the AC pump 45 was rotating at about 8.3 RPM and it uses two rollers 175. This will result in the AC pump 45 occluding the AC tubing 40 about 16.6 times per minute, and the time between each of these pump occlusions will be about 0.06 minutes or about 3.6 seconds. Each release of a pump occlusion of the AC tubing 40 by the rollers 175 of the AC pump 45 reaching the exit 170 will produce a corresponding pressure drop/spike 130 in the waveform 185. These pressure drops/spikes 130 should then also occur about every 3.6 seconds for an occlusion in that portion of the AC tubing 40 which is located between the AC pump 45 and the AC container 35.

Figure 5:
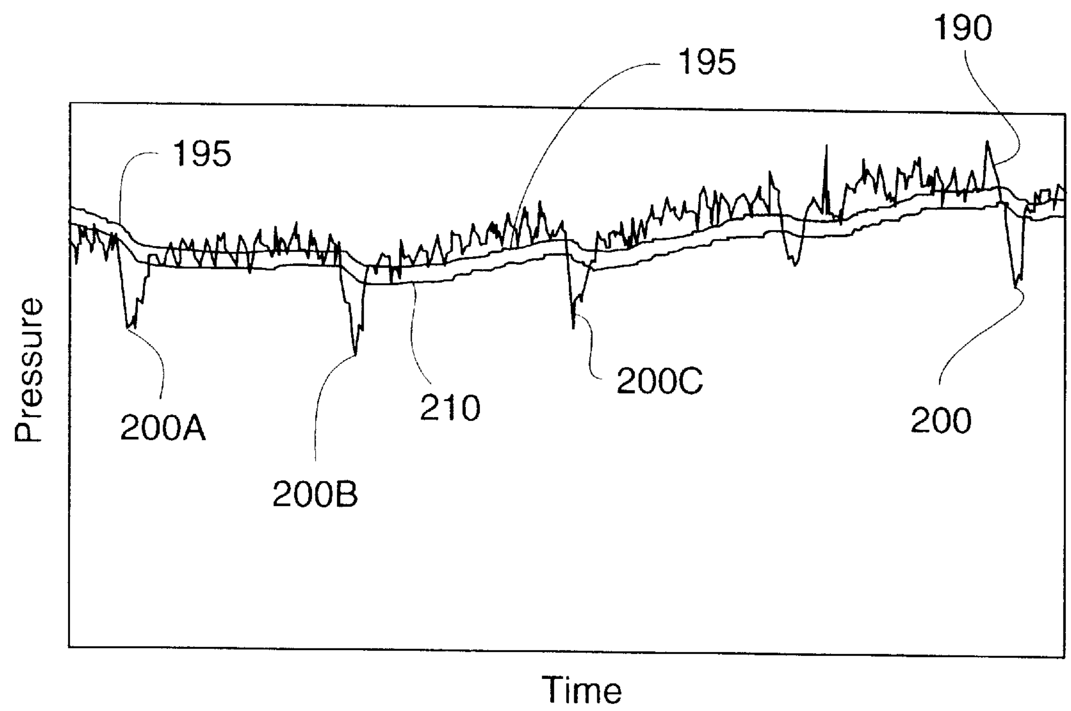
FIG. 5 is another embodiment of a waveform analyzer which may be used by the occlusion monitoring system of FIG. 3.

The waveform analyzer 110 may also be initialized or configured to identify an occluded condition in the manner illustrated in FIG. 5. A waveform 190 corresponds with the pressure being sensed by the pressure sensing device 65 in the blood inlet tubing 25 at the second location 70 during the most recent draw cycle (i.e., when drawing blood from the donor/patient 10). The waveform 190 is produced in the same manner as the waveform 185 discussed above, and is the pressure variation in the inlet tubing 25 at the second location 70, as sensed by the pressure sensing device 65, when there is an occlusion in the AC tubing 40 between the AC pump 45 and the AC container 35 during operation of the AC pump 45. As in the case of the pressure drops/spikes 130 in the case of the waveform 185, a pressure drop/spike 200 in the waveform 190 is created each time one of the rollers 175 of the AC pump 45 releases the pump occlusion in the AC tubing 40.

The waveform analyzer 110 as configured/initialized in FIG. 5 reduces the effects of noise in the blood apheresis system 5, particularly that created by the blood inlet pump 30. That is, the waveform analyzer 110 "processes" the waveform 190 to increase the "sensitivity" of the analyzer 110 in detecting the pressure drops/spikes 200 in the waveform 190. Initially, the waveform analyzer 110 generates a running average waveform 195 which is a running average of the waveform 190. For instance, a plurality of samples of signals from the pressure sensing device 65 may be averaged to provide a data point for generating the running average waveform 195 (e.g., providing the data point from the 40 most current signals from the pressure sensing device 65). The waveform analyzer 110 also creates a threshold waveform 210 which is established at a certain value below the running average waveform 195 (e.g., by estimating the noise from a given set of data, such as from the most current drawing operation, and offsetting the running average waveform 195 by this amount to generate the threshold waveform 210). It should be appreciated that the amplitude and/or form of the waveform 190 may change from one draw cycle to the next. As such, so too will the running average waveform 195 and thus the threshold waveform 210.

Generally, the waveform analyzer 110 identifies an occlusion in the AC tubing 40 between the AC pump 45 and the AC container 35 by noting each time that any portion of the pressure waveform 190 extends below the threshold waveform 210. If the next instance where the pressure waveform 190 extends below the threshold waveform 210 is equal to the inverse of the product of the rotational speed of the AC pump 45 and the number of rollers 175 utilized by the AC pump 45(i.e., the period between pressure drops/spikes 200 is equal to 1/(speed of the pump 45 multiplied by the number of rollers 175)), a signal is sent to the alarm 135 and/or the display 145 to provide an indication to the operator of the apheresis system 5 that an occlusion exists in that portion of the AC tubing 40 which is disposed between the AC pump 45 and the AC container 35. That is, if the time between the pressure drop/spike 200A and the pressure drop/spike 200B is equal to the period of the AC pump 45 (i.e., the inverse of the frequency of the pump 45 which is the rotational speed of the pump 45 multiplied by the number of rollers used by the AC pump 45), the waveform analyzer 110 will identify this as an occlusion condition for the AC tubing 40. If a time period between the pressure drop/spike 200A and pressure drop/spike 200B is less than or exceeds the inverse of the product of the speed of the pump 45 and the number of its rollers 175, the waveform analyzer 110 may be reinitialized for purposes of looking for an occlusion in the AC tubing 40. Specifically, the waveform analyzer 110 may be reinitialized to evaluate the time period between the pressure drop/spike 200B and the next pressure drop/spike 200 which exceeds the threshold waveform 210 (i.e., the pressure drop/spike 200C) to evaluate for occlusions in the above-noted manner.

The ability to accurately detect pressure drops/spikes in a waveform generated from the pressure sensing device 65 is not affected by the speed of the inlet pump 30 and/or the AC pump 45 (within ranges normally used in an apheresis procedure) in the case of the techniques referred to in FIGS. 4–5. That is, the ability of the waveform analyzer 110 to detect a pattern of pressure drops/spikes indicative of or corresponding with an occlusion in the AC tubing 40 between the AC container 35 and the AC pump 45 is not adversely affected by the speed selected for the inlet pump 30 and/or the AC pump 45. Other signal processing techniques may be affected by the speed which is selected for the blood inlet pump 30 and the AC pump 45. For instance, if a synchronized average detection technique is used to process the signal from the pressure sensing device 65, running the AC pump 45 at the exact speed of the blood inlet pump 30, or an exact multiple thereof, may present a problem which would have to be addressed to realize sufficiently reliable occlusion monitoring.

The above-described principles may be used to detect a situation where there is a substantially 100% occlusion in the AC tubing 40 somewhere between the AC pump 45 and the AC container 35 (i.e., a "no flow" condition from the AC container 35 to the AC pump 45). The above-noted "simple detection technique" of FIG. 4 may detect these 100% occlusions. However, by "processing" the signal from the pressure sensing device 65, such as by using the technique presented in FIG. 5, synchronized average detection, or adaptive filtering techniques, less than 100% occlusions may be detected in that portion of the AC tubing 40 between the AC pump 45 and the AC container 35. Specifically, in one embodiment occlusions of this same AC tubing 40 which reduce the flow by only about 50% (50% occlusions) may be detected by the AC occlusion monitoring system 60. In another embodiment, occlusions of this same AC tubing 40 may be detected by the AC occlusion monitoring stems 60 in which the flow through the AC tubing 40 has only been reduced by at least about 28% (i.e., at least a 28% occlusion in the noted portion of the AC tubing 40). Moreover, the above-described principles may be incorporated into other blood apheresis systems, such as the COBE Spectra™ system which is commercially available from the assignee of this patent application.

The foregoing description of the invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain best modes known of practicing the invention and to enable others skilled in the art to utilize the invention in such, or other, embodiments and with the various modifications required by the particular applications or uses of the invention. It is intended that the appended claims be construed to include alternative embodiments to the extent permitted by the prior art.

What is claimed is:

1. A method of monitoring for occlusion of a conduit in a flow circuit, said flow circuit comprising a first conduit having a flow therethrough, a fluid supply, a second conduit extending between said fluid supply and a first location on said first conduit at which said first and second conduits are fluidly connected, and a pump disposed between said first location and said fluid supply and interfacing with said second conduit, said method comprising the steps of:

pumping a fluid from said fluid supply through said second conduit and into said first conduit using said pump;

monitoring a pressure in said first conduit at a second location; and monitoring for an occlusion of any portion of said second conduit disposed between said fluid supply and said pump using said monitoring a pressure step.

2. A method, as claimed in claim 1, wherein:

said pump is a peristaltic pump comprising at least one roller and said pumping a fluid step comprises progressively occluding said second conduit with said at least one roller.

3. A method, as claimed in claim 1, wherein:

said pumping a fluid step comprises at least periodically substantially isolating said fluid supply from said first conduit.

4. A method, as claimed in claim 1, wherein:

said monitoring a pressure step is performed downstream of said first location, wherein said second location is displaced from said first location.

5. A method, as claimed in claim 1, wherein:

said monitoring a pressure step comprises generating a waveform corresponding with a pressure in said first conduit at said second location.

6. A method, as claimed in claim 1, wherein:

said monitoring a pressure step comprises generating a signal corresponding with a pressure in said first conduit at said second location and processing said signal to account for at least noise in at least part of said flow circuit.

7. A method, as claimed in claim 1, wherein:

said monitoring a pressure step comprises generating a computer-readable signal corresponding with a pressure in said first conduit at said second location.

8. A method, as claimed in claim 1, wherein:

said monitoring for an occlusion step comprises monitoring for a pattern of a plurality of negative pressure spikes of at least a certain magnitude from said monitoring a pressure step.

9. A method, as claimed in claim 1, wherein:

said monitoring for an occlusion step comprises monitoring for a pattern of a plurality of negative pressure spikes, each having at least a certain magnitude and a predetermined width.

10. A method, as claimed in claim 1, wherein:

said pumping a fluid step comprises sequentially and progressively occluding said second conduit using a plurality of spaced rollers of a peristaltic pump, said monitoring for an occlusion step comprising monitoring for a pressure waveform in which there are a plurality of negative pressure spikes of at least a certain magnitude, a time between adjacent said negative pressure spikes corresponding with a time which is equal to an inverse of a product of a rotational speed of said peristaltic pump and a number of said rollers used by said peristaltic pump.

11. A method, as claimed in claim 10, further comprising the step of:

introducing a first occlusion in a portion of said second conduit between said pump and said fluid supply and generating a negative pressure in a portion of said second conduit between one of said rollers performing said occluding step and said first occlusion in said second conduit, wherein said pumping step further comprises the step of sequentially releasing an occlusion in said second conduit, said method further comprising the step of drawing fluid from said first conduit and a portion of said second conduit between said pump and said first location toward said first occlusion in said second conduit after each said releasing step and using said generating step, each said drawing step producing a corresponding pressure drop at said second location to produce one of said pressure spikes.

12. A method, as claimed in claim 1, wherein:

said monitoring for an occlusion step comprises detecting a substantially 100% occlusion in said second conduit between said pump and said fluid supply.

13. A method, as claimed in claim 1, wherein:

said monitoring for an occlusion step comprises detecting at least about a 50% occlusion in said second conduit between said pump and said fluid supply.

14. A method, as claimed in claim 1, wherein:

said monitoring for an occlusion step comprises detecting at least about a 28% occlusion in said second conduit between said pump and said fluid supply.

15. A method, as claimed in claim 1, further comprising the step of:

providing an alarm when an occlusion in any portion of said second conduit disposed between said fluid supply and said pump is identified from said monitoring for an occlusion step.

16. A method of monitoring for occlusion of a conduit in an extracorporeal blood processing system, said blood processing system comprising a blood supply, a blood processing device, a blood inlet conduit extending between said blood supply and said blood processing device, a blood inlet pump disposed between said blood supply and said blood processing device and interfacing with said blood inlet conduit at a first location, an anticoagulant supply, an anticoagulant conduit extending between said anticoagulant supply and a second location on said blood inlet conduit at which said blood inlet conduit and said anticoagulant conduit are fluidly connected, and an anticoagulant pump disposed between said second location and said anticoagulant supply and interfacing with said anticoagulant conduit, said method comprising the steps of:

pumping blood from said blood supply to said blood processing device through said blood inlet conduit using said blood inlet pump;

pumping anticoagulant from said anticoagulant supply through said anticoagulant conduit and into said blood inlet conduit using said anticoagulant pump;

monitoring a pressure in said blood inlet conduit at a third location; and monitoring for an occlusion of any portion of said anticoagulant conduit located between said anticoagulant supply and said anticoagulant pump using said monitoring a pressure step.

17. A method, as claimed in claim 16, wherein:

said anticoagulant pump is a peristaltic pump comprising at least one roller and said pumping anticoagulant step comprises progressively occluding said anticoagulant conduit with said at least one roller.

18. A method, as claimed in claim 16, wherein:

said pumping anticoagulant step comprises at least periodically substantially isolating said anticoagulant supply from said blood inlet conduit.

19. A method, as claimed in claim 16, wherein:

said third location is located between said first location and said second location.

20. A method, as claimed in claim 16, wherein:

said monitoring a pressure step comprises generating a waveform corresponding with a pressure in said blood inlet conduit at said third location.

21. A method, as claimed in claim 16, wherein:

said monitoring a pressure step comprises generating a signal corresponding with a pressure in said blood inlet conduit at said third location and processing said signal to account for at least noise due to said blood inlet pump.

22. A method, as claimed in claim 16, wherein:

said monitoring a pressure step comprises generating a computer-readable signal corresponding with a pressure in said blood inlet conduit at said third location.

23. A method, as claimed in claim 16, wherein:

said monitoring for an occlusion step comprises monitoring for a pattern of a plurality of negative pressure spikes of at least a certain magnitude from said monitoring a pressure step.

24. A method, as claimed in claim 16, wherein:

said monitoring for an occlusion step comprises monitoring for a certain pattern of a plurality of negative pressure spikes, each having at least a certain magnitude and a predetermined width.

25. A method, as claimed in claim 16, wherein:

said pumping anticoagulant step comprises sequentially and progressively occluding said anticoagulant conduit using a plurality of spaced rollers of said anticoagulant pump, said monitoring for an occlusion step comprising monitoring for a certain pressure versus time waveform in which there are a plurality of negative pressure spikes of at least a certain magnitude, a time between adjacent said negative pressure spikes corresponding with a time which is equal to an inverse of a product of a rotational speed of said anticoagulant pump and a number of said rollers used by said anticoagulant pump.

26. A method, as claimed in claim 25, further comprising the step of:

introducing a first occlusion in a portion of said anticoagulant conduit between said anticoagulant pump and said anticoagulant supply and generating a negative pressure in a portion of said anticoagulant conduit between one of said rollers performing said occluding step and said first occlusion in said anticoagulant conduit, wherein said pumping anticoagulant step further comprises the step of sequentially releasing an occlusion in said anticoagulant conduit, said method further comprising the step of drawing fluid from said blood inlet conduit and a portion of said anticoagulant conduit between said anticoagulant pump and said second location toward said first occlusion in said anticoagulant conduit after each said releasing step and using said generating step, each said drawing step producing a corresponding pressure drop at said third location to produce one of said pressure spikes.

27. A method, as claimed in claim 16, wherein:

said monitoring for an occlusion step comprises detecting at least about a 50% occlusion in said anticoagulant conduit between said anticoagulant pump and said anticoagulant supply.

28. A method, as claimed in claim 16, further comprising the step of:

providing an alarm when an occlusion in any portion of said anticoagulant conduit disposed between said anticoagulant supply and said anticoagulant pump is identified from said monitoring for an occlusion step.

29. A flow circuit, comprising:

a first conduit;

a fluid supply;

a second conduit extending between said fluid supply and a first location on said first conduit at which said first and second conduits are fluidly connected;

a pump disposed between said first location on said first conduit and said fluid supply and interfacing with said second conduit;

a pressure sensing device interfacing with said first conduit at a second location; and means for monitoring for an occlusion of any portion of said second conduit disposed between said fluid supply and said pump, said means for monitoring comprising said pressure sensing device.

30. A flow circuit, as claimed in claim 29, wherein:

said pump is a peristaltic pump comprising at least one roller which progressively occludes said second conduit.

31. A flow circuit, as claimed in claim 29, further comprising:

means for periodically substantially isolating said fluid supply from said first conduit, said means for periodically substantially isolating comprising said pump.

32. A flow circuit, as claimed in claim 29, wherein:

said second location is downstream of said first location.

33. A flow circuit, as claimed in claim 29, wherein:

said means for monitoring comprises means for generating a waveform corresponding with a pressure in said first conduit at said second location.

34. A flow circuit, as claimed in claim 33, wherein:

said means for monitoring comprises means for monitoring said waveform for a pattern of a plurality of negative pressure spikes of at least a certain magnitude.

35. A flow circuit, as claimed in claim 33, wherein:

said means for monitoring comprises means for monitoring said waveform for a pattern of a plurality of negative pressure spikes, each having at least a certain magnitude and a predetermined width.

36. A flow circuit, as claimed in claim 33, wherein:

said pump comprises a peristaltic pump with a plurality of rollers which sequentially, progressively occlude said second conduit, said means for monitoring comprising means for monitoring said waveform for a plurality of negative pressure spikes of at least a certain magnitude, a time between adjacent said negative pressure spikes corresponding with a time which is equal to an inverse of a product of a rotational speed of said peristaltic pump and a number of said rollers used by said peristaltic pump.

37. A flow circuit, as claimed in claim 33, wherein:

said means for monitoring comprises means for monitoring said waveform for a pattern of a plurality of negative pressure spikes and means for accentuating said negative pressure spikes.

38. A flow circuit, as claimed in claim 29, wherein:

said means for monitoring comprises means for generating a signal corresponding with a pressure in said first conduit at said second location and means for processing said signal to account for at least noise in at least part of said flow circuit.

39. A flow circuit, as claimed in claim 29, wherein:

said means for monitoring comprises means for generating a computer-readable signal corresponding with a pressure in said first conduit at said second location.

40. A flow circuit, as claimed in claim 29, further comprising:

an alarm interconnected with said means for monitoring, wherein said alarm is activated when an occlusion in any portion of said second conduit disposed between said fluid supply and said pump is identified by said means for monitoring.

* * * * *

UNITED STATES PATENT AND TRADEMARK OFFICE

CERTIFICATE OF CORRECTION

PATENT NO. : 5,906,589

DATED : May 25, 1999

INVENTOR(S) : Gordon et al.

It is certified that error appears in the above-indentified patent and that said Letters Patent is hereby corrected as shown below:

On the title page, item [75], first line, on the front of the Patent, please delete the word "Lakewood" and insert therefor - Littleton -

Signed and Sealed this

Eighteenth Day of January, 2000

Attest:

Q. TODD DICKINSON

Attesting Officer

*Commissioner of Patents and Trademarks*